(12) United States Patent
Bontempelli et al.

(10) Patent No.: US 8,329,947 B2
(45) Date of Patent: Dec. 11, 2012

(54) PROCESS FOR THE SYNTHESIS OF AGOMELATINE

(75) Inventors: Pascal Bontempelli, Beuzeville-la-Grenier (FR); Xavier Jalenques, Saint Aubin de Cretot (FR); Jerome-Benoit Starck, Rueil-Malmaison (FR); Jean-Pierre Sery, Pissy-Poville (FR)

(73) Assignee: Les Laboratoires Servier, Suresnes Cedex (FR)

( * ) Notice: Subject to any disclaimer, the term of this patent is extended or adjusted under 35 U.S.C. 154(b) by 539 days.

(21) Appl. No.: 12/462,363

(22) Filed: Aug. 3, 2009

(65) Prior Publication Data
US 2010/0036161 A1    Feb. 11, 2010

(30) Foreign Application Priority Data
Aug. 5, 2008   (FR) ..................... 08 04463

(51) Int. Cl.
*C07C 231/06*    (2006.01)
(52) U.S. Cl. ....................... 564/126; 564/124
(58) Field of Classification Search ............ 564/124, 564/126
See application file for complete search history.

(56) References Cited

U.S. PATENT DOCUMENTS
3,062,869 A      11/1962   Gould et al.
2005/0182276 A1*  8/2005   Souvie et al. ................. 564/123

FOREIGN PATENT DOCUMENTS
EP    1564202    8/2005
FR    1141276    8/1957

OTHER PUBLICATIONS
W.H. Carothers, et al., "The preparation of some primary amines by the catalytic reduction of nitriles" Journal of the American Chemical Society, vol. 47, No. 12, p. 3051-3057, 1925.
French Preliminary Search Report for FR0804463 of Mar. 11, 2009.

* cited by examiner

*Primary Examiner* — Shailendra Kumar
(74) *Attorney, Agent, or Firm* — Hueschen and Sage

(57) ABSTRACT

Process for the industrial synthesis of the compound of formula (I)

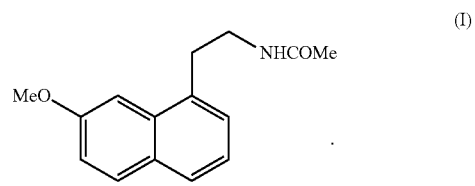

5 Claims, No Drawings

PROCESS FOR THE SYNTHESIS OF AGOMELATINE

The present invention relates to a new process for the industrial synthesis of agomelatine, or N-[2-(7-methoxy-1-naphthyl)ethyl]acetamide, of formula (I):

(I)

Agomelatine, or N-[2-(7-methoxy-1-naphthyl)ethyl]acetamide, has valuable pharmacological properties.

It has, in fact, the double characteristic of being, on the one hand, an agonist of receptors of the melatoninergic system and, on the other hand, an antagonist of the 5-$HT_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent specifications EP 0 447 285 and EP 1 564 202.

In view of the pharmaceutical value of this compound, it has been important to be able to produce it using an effective industrial synthesis process which is readily transferable to the industrial scale and which provides agomelatine in a good yield and with excellent purity.

Patent specification EP 0 447 285 describes production of agomelatine in eight steps starting from 7-methoxy-1-tetralone, in an average yield of less than 30%.

In Patent specification EP 1 564 202, the Applicant developed a new, much more effective and industrialisable synthesis route in only four steps that makes it possible to obtain agomelatine in highly reproducible manner in a well-defined crystalline form.

The Applicant has now continued his investigations and developed a new process for the synthesis of agomelatine that is even more effective than that described in the prior art: agomelatine is obtained directly starting from (7-methoxy-1-naphthyl)acetonitrile, which makes it possible to achieve complete synthesis in only three steps starting from 7-methoxy-1-tetralone. This new process makes it possible to obtain agomelatine in reproducible manner and without requiring laborious purification, with a purity that is compatible with its use as a pharmaceutical active ingredient.

Saving one or more steps in a synthesis process is always desirable to industry because it allows a time saving, a gain in yield and, consequently, a lower final cost. However, reducing the number of steps in a synthesis procedure is not a trivial exercise, especially when industrial quantities are involved: two steps combined into one involve an increase in the number and amounts of reagents present and, owing to the increased complexity of the mixture, purification of the reaction product becomes more difficult. Finally, the probability of secondary products appearing because of the greater number of reagents that are present at the same time is very high.

The Applicant has now developed an industrial process which makes it possible to obtain agomelatine directly, starting from (7-methoxy-1-naphthyl)acetonitrile.

More specifically, the present invention relates to a process for the industrial synthesis of the compound of formula (I):

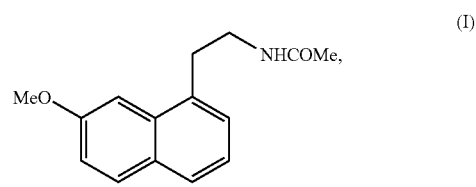
(I)

which process is characterised in that there is reacted (7-methoxy-1-naphthyl)acetonitrile of formula (II):

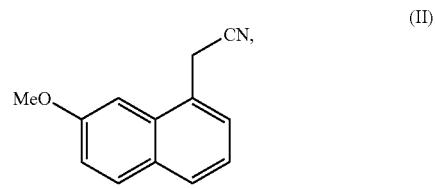
(II)

which is subjected to reduction by hydrogen in the presence of Raney nickel in a medium comprising acetic anhydride in a polar protic medium to yield the compound of formula (I), which is isolated in the form of a solid.

The compound of formula (II) is obtained by customary reactions of organic chemistry. The compound of formula (II) can, for example, be obtained by condensation of cyanoacetic acid with 7-methoxy-tetralone followed by oxidation of the condensation product, as described in Patent specifications EP1564204 and EP1564205.

Preferably, conversion of the compound of formula (II) into the compound of formula (I) according to the invention is carried out under a minimum pressure of 5 bars and, more preferably, is carried out using a pressure of from 10 bars to 50 bars of hydrogen.

Advantageously, conversion of the compound of formula (II) into the compound of formula (I) according to the invention is carried out at from 25° C. to 90° C. and, more especially, from 50° C. to 70° C.

The amount of Raney nickel used in the reaction converting the compound of formula (II) into the compound of formula (I) is at least 5% by weight and, more preferably, from 10% to 20% by weight.

The reaction medium for the reaction converting the compound of formula (II) into the compound of formula (I) preferably comprises one or more polar protic solvents such as ethanol, acetic acid and/or water, and more preferably ethanol and/or water. Optionally, the reaction medium additionally contains sodium acetate.

This process is especially valuable for the following reasons:

it makes it possible to obtain the compound of formula (I) on an industrial scale in a single step, starting from (7-methoxy-1-naphthyl)acetonitrile, in excellent yields of more than 85%; this new process accordingly allows the compound of formula (I) to be produced in only 3 steps starting from 7-methoxy-tetralone;

the compound of formula (I) obtained has, in reproducible manner, the characteristics of the crystalline form described in Patent specification EP1564202;

the operating conditions that have been developed make it possible to minimise formation of the major secondary product of the reaction: N,N-bis[2-(7-methoxy-1-naphthyl)ethyl]acetamide, which originates from dimerisation between two reaction intermediates; a priori it was in fact very difficult—in view of the very existence of this secondary reaction which dramatically increases in magnitude when the reaction is carried out as a "one-pot" reaction—to envisage directly obtaining the compound of formula (I) starting from (7-methoxy-1-naphthyl)acetonitrile under purity conditions that are compatible with its subsequent pharmaceutical use; lengthy and highly detailed studies of the operating conditions were necessary in order to arrive at an impurity level for the dimerised compound that is acceptable for subsequent use of the compound of formula (I) as a medicament.

The Examples hereinbelow illustrate the invention but do not limit it in any way.

EXAMPLE 1

N-[2-(7-Methoxy-1-naphthyl)ethyl]acetamide

Step A: (7-Methoxy-3,4-dihydro-1-naphthyl)acetonitrile

There are introduced into a 670 litre reactor 85.0 kg of 7-methoxy-1-tetralone, 60.3 kg of cyanoacetic acid and 15.6 kg of heptanoic acid in toluene in the presence of 12.7 kg of benzylamine (or 11.0 kg of aniline). The mixture is heated at reflux. When all the starting substrate has disappeared, the solution is cooled and filtered. The precipitate obtained is washed with toluene and then the filtrate obtained is washed with 2N sodium hydroxide solution and then with water until neutrality. After evaporating off the solvent, the solid obtained is recrystallised from an ethanol/water (80/20) mixture to yield the title product in a yield of 90% and with a chemical purity of more than 99%.

Melting point: 48-50° C.

Step B: (7-Methoxy-1-naphthyl)acetonitrile

There are introduced into a 670 litre reactor 12.6 kg of 5% palladium-on-carbon in toluene, which is heated at reflux; then 96.1 kg of (7-methoxy-3,4-dihydro-1-naphthyl)acetonitrile dissolved in toluene are added and also 63.7 kg of allyl methacrylate. The reaction is continued at reflux and is monitored by vapour phase chromatography. When all the starting substrate has disappeared, the reaction mixture is cooled to ambient temperature and then filtered. After evaporating off the toluene, the solid residue obtained is recrystallised from an ethanol/water (80/20) mixture to yield the title product in a yield of 91% and with a chemical purity of more than 99%.

Melting point: 83° C.

Step C: N-[2-(7-Methoxy-1-naphthyl)ethyl]acetamide

There are introduced into an 8 litre reactor 136 g of Raney nickel, 2.06 litres of ethanol and 0.23 litre of water. Whilst stirring at 70° C. and under 30 bars of hydrogen, the compound obtained in Step B (0.8 kg), dissolved in acetic anhydride (2.4 litres), is added slowly. At the end of the addition, the reaction mixture is stirred for 1 hour under hydrogen at 30 bars; the reactor is then subjected to decompression and the liquors are filtered. After concentrating the mixture, the residue is crystallised from an ethanol/water 35/65 mixture to yield the title product in a yield of 89% and with a chemical purity of more than 99%.

Melting point: 108° C.

EXAMPLE 2

Determination of the Crystalline Form of the Compound N-[2-7-methoxy-1-naphthyl)ethyl]acetamide Obtained in Example 1

Data recording was carried out using the D8 high-resolution diffractometer from Bruker AXS with the following parameters: an angular range of 3°-90° in terms of 2θ, a step of 0.01° and 30 s per step. The N-[2-(7-methoxy-1-naphthyl)ethyl]acetamide powder obtained in Example 1 was deposited on a transmission mounting support. The X-ray source is a copper tube ($\lambda CuK_{\alpha 1}$=1.54056 Å). The mounting includes a front monochromator (Ge(111) crystal) and an energy-resolved solid-state detector (MXP-D1, Moxtec-SEPH). The compound is well crystallised: the line width at half-height is of the order of 0.07° in terms of 2θ.

The following parameters were accordingly determined:

crystal structure of unit cell: monoclinic, unit cell parameters: a=20.0903 Å, b=9.3194 Å, c=15.4796 Å, β=108.667° space group: $P2_1/n$ number of molecules in the unit cell: 8 volume of the unit cell: $V_{unit\ cell}$=2746.742 Å$^3$ density: d=1.13 g/cm$^3$.

EXAMPLE 3

Determination, by Means of the X-ray Powder Diffraction Diagram, of the Crystalline Form of the N-[2-7-methoxy-1-naphthyl)ethyl]acetamide Compound Obtained in Example 1

The crystalline form of the compound obtained in Example 1 is characterised by the following X-ray powder diffraction diagram, measured using a Siemens D5005 diffractometer (copper anticathode) and expressed in terms of interplanar distance d, Bragg's angle 2 theta, and relative intensity (expressed as a percentage in relation to the most intense line):

| Angle 2 theta (°) | Interplanar distance d (Å) | Intensity (%) |
|---|---|---|
| 9.26 | 9.544 | 23 |
| 10.50 | 8.419 | 13 |
| 15.34 | 5.771 | 24 |
| 17.15 | 5.165 | 100 |

The invention claimed is:

1. A process for the synthesis of a compound of formula (I)

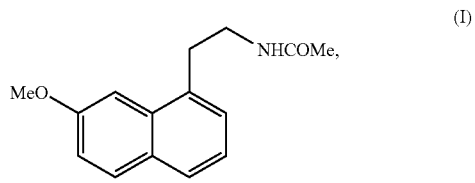

wherein (7-methoxy-1-naphthyl)acetonitrile of formula (II):

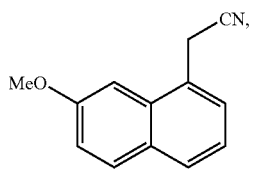

is subjected to reduction by hydrogen in the presence of Raney nickel in a medium comprising acetic anhydride in a polar protic medium to yield the compound of formula (I), which is isolated in the form of a solid.

2. The process of claim 1, wherein the reaction is carried out under a pressure of from 10 bars to 50 bars of hydrogen.

3. The process of claim 1, wherein the reaction is carried out at from 25° C. to 90° C.

4. The process of claim 1, wherein the amount of Raney nickel used in the reaction is from 10% to 20% by weight.

5. The process of claim 1, wherein the reaction medium for the reaction comprises ethanol and/or water.

* * * * *